United States Patent [19]

Kiyama et al.

[11] Patent Number: 4,968,823

[45] Date of Patent: Nov. 6, 1990

[54] PROCESS FOR THE FRACTIONAL PRODUCTION OF ALKYTIN OXIDE

[75] Inventors: Aiichiro Kiyama, Oita; Hitoshi Kawaguchi, Fukuoka; Yoshikazu Nakajima, Oita, all of Japan

[73] Assignees: Yoshitomi Pharmaceutical Industries, Ltd.; M & T Yoshitomi Chemicals, Ltd., both of Osaka, Japan

[21] Appl. No.: 341,982

[22] Filed: Apr. 24, 1989

Related U.S. Application Data

[63] Continuation-in-part of Ser. No. 7/216,572, Jul. 8, 1988, abandoned.

[51] Int. Cl.$^5$ .............................................. C07F 7/72
[52] U.S. Cl. ...................................... 556/88; 556/89; 556/95
[58] Field of Search ............................. 556/88, 89, 95

[56] References Cited

U.S. PATENT DOCUMENTS

| | | | |
|---|---|---|---|
| 2,718,522 | 9/1955 | Gloskey | 260/429 |
| 2,867,642 | 1/1959 | Ramsden et al. | 260/429.7 |
| 2,868,820 | 1/1959 | Nitzsche et al. | 260/429.7 |
| 2,957,785 | 10/1960 | Leatherland | 117/138.5 |
| 3,390,159 | 6/1968 | Katsumura et al. | |
| 3,402,189 | 9/1968 | Natoli | 260/429 |
| 3,466,311 | 9/1969 | Mizuno et al. | |
| 3,470,221 | 9/1969 | Chadha et al. | 260/429.7 |
| 3,547,965 | 12/1970 | Takubo et al. | 260/429 |
| 4,173,346 | 11/1979 | Collins et al. | 260/429.7 |

FOREIGN PATENT DOCUMENTS

| | | | |
|---|---|---|---|
| 1170229 | 12/1956 | France | 556/88 |
| 1515649 | 3/1967 | France | 556/88 |
| 2041467 | 1/1971 | France | 556/88 |
| 6046 | 6/1968 | Japan | 556/88 |
| 7090 | 2/1973 | Japan | 556/88 |
| 30717 | 8/1980 | Japan | 556/88 |

OTHER PUBLICATIONS

Chemical Abstracts 85,33189B, Kiss et al., "Alkyltin oxides", Nov. 15, 1975.
Chemical Abstracts 86,106785a, Masuda, "Granulation of Monoalkyltin acids", Apr. 9, 1975.
"Investigations on Organic Compounds XXII", 1966, pp. 873–878, J. G. A. Luuten.

*Primary Examiner*—Paul F. Shaver
*Attorney, Agent, or Firm*—Sughrue, Mion, Zinn, Macpeak & Seas

[57] ABSTRACT

A process for the fractional production of alkyltin oxides which comprises the steps of:

subjecting a mono-, di- or trialkyltin halide to continuous hydrolysis at a temperature between 30° to 100° C. for a period of 10 minutes to 3 hours by the use of a 1% to 50% aqueous solution of a basic substance, thereby forming in the hydrolysis reaction mixture a dialkyltin oxide having an average particle diameter of 10 μm or more, provided that where an intended alkyltin oxide is solid, the continuous hydrolysis is performed in the presence of an organic solvent slightly soluble in water and having a boiling point as measured under ordinary pressure of 150° C. or lower and a specific gravity of 1.1 or smaller;

allowing the resulting reaction mixture to stand, thereby to form three phases composed of an organic phase, an aqueous phase, and a phase consisting substantially of the dialkyltin oxide and having a specific gravity 0.02 or more larger than that of the aqueous phase;

separating the three phases from one another; and isolating a bis(trialkyltin) oxide or a trialkyltin hydroxide from the organic phase, a monoalkyltin oxide from the aqueous phase, and the dialkyltin oxide from the phase consisting substantially of the dialkyltin oxide and having a specific gravity 0.02 or more larger than that of the aqueous phase.

1 Claim, 5 Drawing Sheets

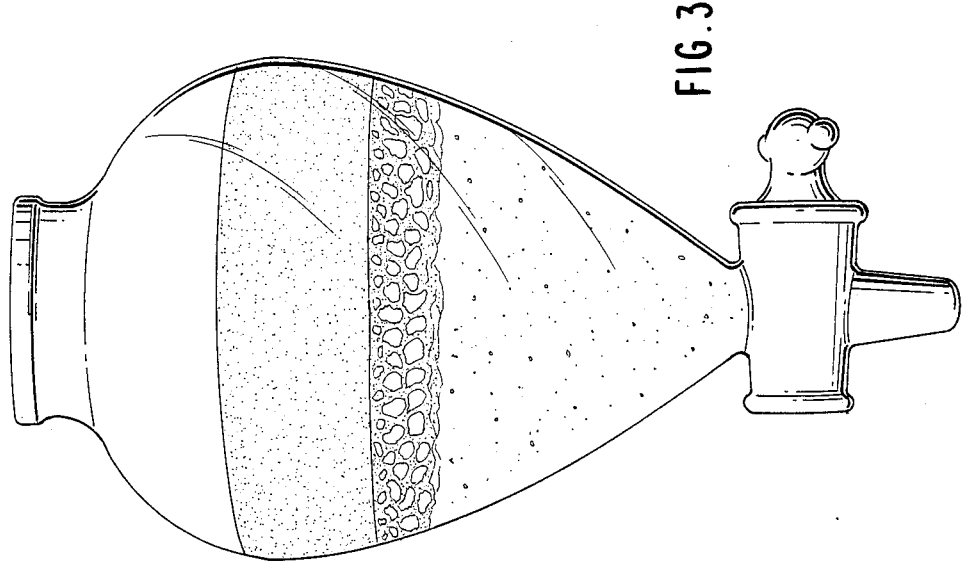
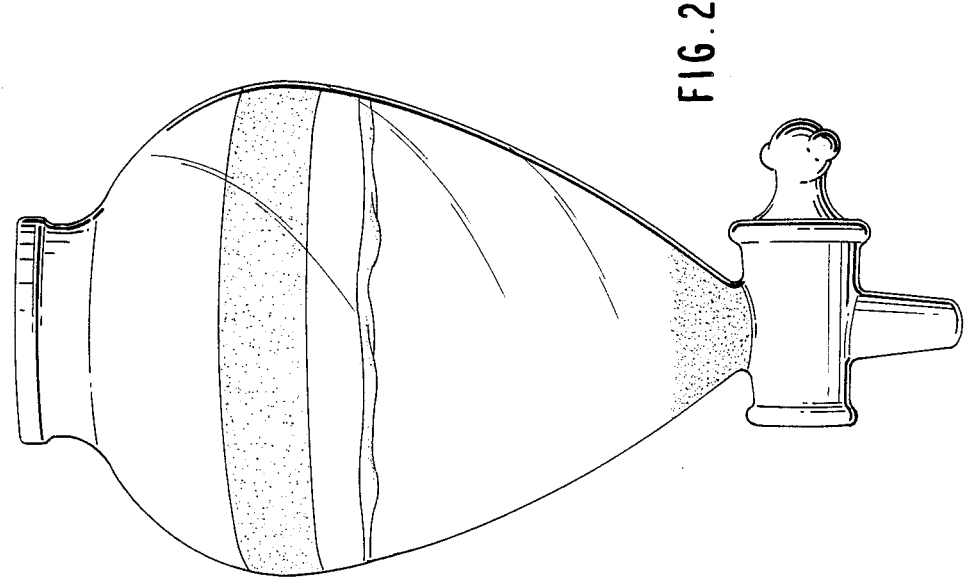

PROCESS FOR THE FRACTIONAL PRODUCTION OF ALKYTIN OXIDE

This application is a continuation-in-part application of Ser. No. 07/216,572 filed on Jul. 8, 1988, now abandoned.

BACKGROUND OF THE INVENTION

Mono- and dialkyltin oxides are industrially of great value and are being used in large quantities in the productions of stabilizers for polyvinyl chloride resins, catalysts for organic syntheses and catalysts for cationic electrodeposition coating, whereas bis(trialkyltin) oxides or trialkyltin hydroxides (hereinafter, both being put together and referred to as "trialkyltin oxides") hold an important position in the field of antifouling paints. So far, these alkyltin oxides have been produced generally by the method as described, for example, in U.S. Pat. Nos. 2,718,522 and 3,390,159. That is, an alkyltin halide is batch-wise hydrolyzed with a strongly basic substance, such as an alkali metal hydroxide or ammonium hydroxide, in the presence of an organic solvent, thereby to form two phases composed of an aqueous phase containing salts and, in some cases, an alkali metal salt of a monoalkyltin oxide and an organic phase containing a di- and trialkyltin oxides, subsequently the organic phase is separated from the aqueous phase, and then the di- or trialkyltin oxide is isolated from the organic phase by mechanical means, such as filtration or centrifugation.

However, such production process has serious problems from the viewpoints of worker's safety and health, environment, and economical production equipment. That is, the dialkyltin oxide is present in the organic phase in the form of very finely dispersed particles generally having an average particle diameter of 10 $\mu$m or less and, further, these particles are easily compressed with application of pressure thereon, whereby independence of the particles is destroyed. Hence, the isolation of such dialkyltin oxide takes a long time if performed by a pressure-utilizing means, such as filtration or centrifugation, and causes a very large amount of the solvent or the trialkyltin oxide to be vapolised during the isolation. For example, in the case of the production of a trialkyltin oxide, since the corresponding dialkyltin oxide is formed as a by-product in the form of very minute particles suspended in the resulting liquid trialkyltin oxide, removal of the dialkyltin oxide can be completed only by the use of a filter aid such as acid clay. Further, the dialkyltin oxide thus separated cannot be reused as it is because the filter aid is contained therein, and disposal of the oxide as an industrial waste is difficult. On the other hand, since the aqueous phase containing a monoalkyltin oxide and a salt is difficult to be completely separated from the trialkyltin oxide phase, part of the trialkyltin oxide unavoidably mingles in the aqueous phase and should be removed by extraction with an organic solvent. Moreover, because the adverse influences of trialkyltin oxides on humans and the environment cannot be negligible, the whole manufacturing process should be enclosed in a closed-system. However, a completely enclosed manufacturing process in a closed-system cannot be obtained. Furthermore, the filtering or centrifugial equipment used in the prior art process costs too much.

In the case of di- or monoalkyltin oxides, the conventional production processes have, in principle, the same disadvantages as mentioned above for the case of trialkyltin oxides, but the situation is more complicated since solids are processed in large quantities in the production of di- or monoalkyltin oxides. More particularly, the hydrolysis of a dialkyltin dihalide results in the formation of two phases, namely an aqueous phase containing the corresponding monoalkyltin oxide and an organic phase containing the corresponding tri- and dialkyltin oxides, and then the desired dialkyltin oxide is separated from the organic phase by centrifugation or filtration, or other suitable means. For removing the by-product trialkyltin oxide from the separated dialkyltin oxide, the dialkyltin oxide is washed by suspending it in a solvent and then recovered by filtration or centrifugation, and this procedure is repeated several times. However, in order to completely remove the by-product salt and an alkali metal salt of the monoalkyltin oxide or a salt, it is necessary to wash the dialkyltin oxide obtained above several times with a large quantity of water, each washing being followed by separation by filtration, centrifugation or other suitable means.

The present inventors believed that the disadvantages of the prior art processes are mainly due to the necessity for filtration or centrifugation. They further believed that if the hydrolysis can be performed such that it results in the formation of three phases, i.e., an intermediate aqueous phase, an upper organic phase and a lower dialkyltin oxide phase, not only each phase can be easily separated from the others without filtration or centrifugation but also the production process can be enclosed in a closed-system completely. They have made intensive studies based on the above and, as a result, completed the present invention.

SUMMARY OF THE INVENTION

The basic features of this invention are:

(1) to make a dialkyltin oxide to be formed in the reaction mixture to have larger particle diameters, i.e., increased particle weights, by properly selecting manner of and conditions for the hydrolysis, thereby forming a dialkyltin oxide phase beneath a salt-containing aqueous phase;

(2) to form distinct three phases, i.e., the aqueous phase, a liquid organic phase containing a trialkyltin oxide, the organic phase being positioned on the aqueous phase, and the lower phase containing a dialkyltin oxide and substantially free from a mono- and trialkyltin oxides, by controlling the specific gravity of the aqueous phase; and (3) to separate the three phases from one another and to isolate the mono-, di- and trialkyltin oxides from the respective phases separated.

Accordingly, it is an object of the present invention to provide a process for the fractional production of alkyltin oxides, which makes it possible to easily obtain highly purified products through simplified procedures.

The foregoing and other objects, features and advantages of the present invention will be apparent to those skilled in the art from the following detailed description and appended claim taken in connection with the accompanying drawings in which:

BRIEF DESCRIPTION OF THE DRAWINGS

FIG. 2 is a photograph showing the three phases formed in the process of the present invention, which are composed of an upper bis(tri-n-butyltin) oxide phase, an intermediate aqueous phase containing a salt, and a lower phase consisting substantially of di-n-butyltin oxide;

FIG. 3 is a photograph showing bis(tri-n-butyltin) oxide produced by the method described in U.S. Pat. No. 2,718,522, which shows two phases, the upper phase being turbine due to the di-n-butytin oxide suspended therein;

DETAILED DESCRIPTION OF THE INVENTION

Figure 1A:
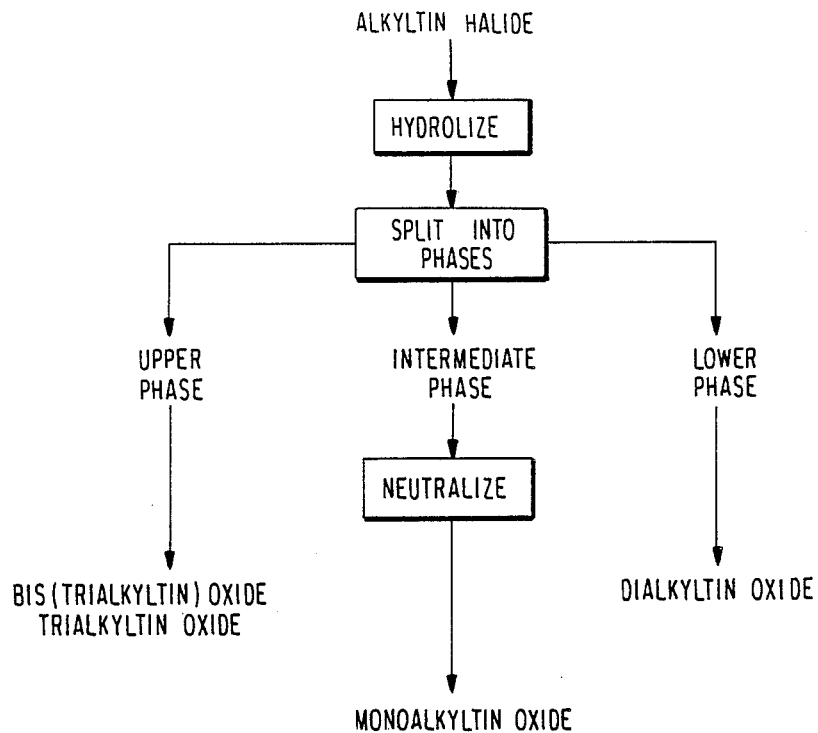
FIG. 1(a) is a flow sheet illustrating the process of the present invention.
Figure 1B:
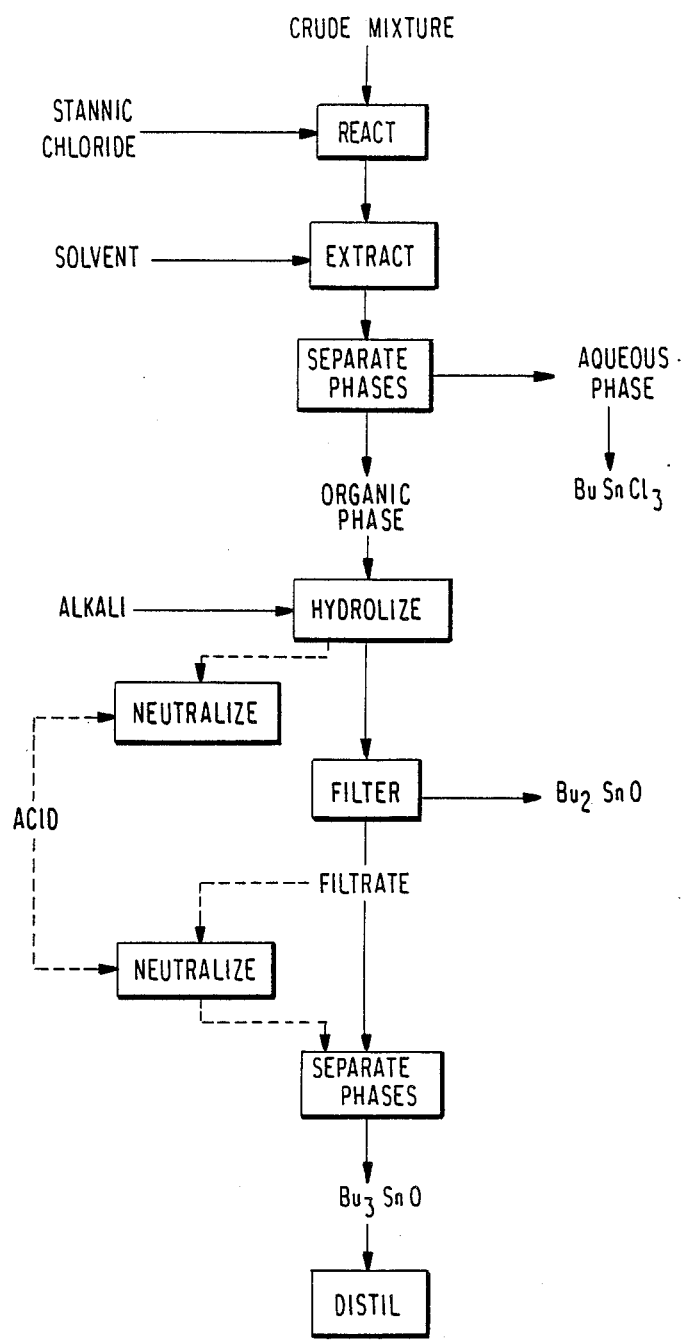
FIG. 1(b) is a flow sheet illustrating the process described in U.S. Pat. No. 2,718,522.

According to the present invention, there is provided a process for the fractional production of alkyltin oxides which comprises the steps of:

subjecting a mono-, di- or trialkyltin halide to continuous hydrolysis at a temperature between 30° to 100° C. for a period of 10 minutes to 3 hours by the use of a 1% to 50% aqueous solution of a basic substance, thereby forming in the hydrolysis reaction mixture a dialkyltin oxide having an average particle diameter of 10 $\mu$m or more, provided that where an intended alkyltin oxide is solid, the continuous hydrolysis is performed in the presence of an organic solvent slightly soluble in water and having a boiling point as measured under ordinary pressure of 150° C. or lower and a specific gravity of 1.1 or smaller;

allowing the resulting reaction mixture to stand, thereby to form three phases composed of an organic phase, an aqueous phase, and a phase consisting substantially of the dialkyltin oxide and having a specific gravity 0.02 or more larger than that of the aqueous phase;

separating the three phases from one another; and isolating a bis(trialkyltin) oxide or a trialkyltin hydroxide from the organic phase, a monoalkyltin oxide from the aqueous phase, and the dialkyltin oxide from the phase consisting substantially of the dialkyltin oxide and having a specific gravity 0.02 or more larger than that of the aqueous phase.

The alkyltin oxides to be produced according to this invention are a monoalkyltin oxide, and/or a dialkyltin oxide, and/or a bis(trialkyltin)oxide or a trialkyltin hydroxide. One or more of these can be obtained, depending on the reaction conditions, in high purity and high quality. The term "alkyl" used herein means an alkyl group having 1 to 8 carbon atoms, such as methyl, ethyl, n-propyl, isopropyl, n-butyl, sec-butyl, tert-butyl, pentyl, isopentyl, neopentyl, n-hexyl, n-heptyl, n-octyl, 2-ethylhexyl, 1,1,3,3-tetramethylbutyl or the like. Of such oxides and hydroxides, industrially valuable are those whose alkyl group is butyl, octyl, etc., such as mono-n-butyltin oxide, di-n-butyltin oxide, di-n-octyltin oxide, bis(tri-n-butyltin) oxide and the like.

The mono-, di- or trialkyltin halide to be used as a starting material is a monoalkyltin trihalide, a dialkyltin dihalide or a trialkyltin halide. Examples of the halides include tri-n-butyltin chloride, di-n-butyltin dibromide, mono-n-butyltin triiodide, di-n-octyltin diiodide and dimethyltin dichloride. However, the halide to be used in this invention is not limited to these. These alkyltin halides usually contain other alkyltin halides and, in some instances, tetraalkyltins. Generally, the contents of such impurities should preferably be about 10% by weight or less, although the content may exceed 10% as long as the impurities do not inhibit or disturb the hydrolysis. In other words, any starting material alkyltin halide having a purity of about 90% or more can usually be employed to give satisfactory results.

The basic substance to be used in the present invention is an alkali metal hydroxide, ammonium hydroxide or the like. Examples of the basic substance include sodium hydroxide, potassium hydroxide and ammonium hydroxide, to which the basic substance is not limited. Of these, sodium hydroxide is particularly advantageous from the industrial viewpoint. This basic substance is usually used in the form of an aqueous solution. The concentration of the basic substance is selected such that the specific gravity of the aqueous salt solution to be formed after the hydrolysis is between the specific gravities of the two phases resulting from the hydrolysis. Generally, the concentrationn is in the range of from 1 to 50% by weight, preferably from 5 to 30% by weight.

The organic solvent is preferably that well dissolving the starting material mono-, di- or trialkyltin halide but not dissolving water and an intended solid alkyltin oxide. Further, since an organic solvent having a relatively high boiling point is disadvantageous for its recovery and reuse, prefered is that having a boiling point of about 150° C. or lower as measured at ordinary pressure. Furthermore, preferred is that having a specific gravity smaller than that of the aqueous salt solution to be formed after the hydrolysis, and specifically that having a specific gravity of 1.1 or smaller. Examples of the organic solvent include benzene, toluene, xylene, pentane, hexane, isohexane, heptane, octane, isooctane, cyclohexane, methylcyclohexane, methyl isobutyl ketone, petroleum ether, petroleum benzine, ligroin, petroleum naphtha, ethylbenzene, n-butanol, isobutanol, sec-butanol, tert-butanol, pentanol, isopentanol, hexanol, heptanol, cyclohexanol, monochlorobenzene, dichloropropane, butyl chloride, amyl chloride and the like. However, the organic solvent is not limited to these compounds. Of the above-mentioned compounds, preferred are hydrocarbons such as heptane, toluene, xylene and the like. These solvents are used alone or in combination thereof. As mentioned hereinbefore, in the process of the present invention , a phase containing a dialkyltin oxide and substantially free from a mono- and trialkyltin oxides is formed beneath the salt-containing aqueous phase by increasing the diameters of dialkyltin oxide particles formed in the hydrolysis reaction mixture and thus increasing their weights, which is one of the basic features of this invention. In order to successfully form the lower phase, the hydrolysis should be performed continuously and the reaction products should be taken out of the reaction system continuously. The reaction time, or residence time, is preferably in the range of from 10 minutes to 3 hours, more preferably from 10 minutes to 1 hour. The reaction temperature preferably between 30° to 100° C., more preferably between 50° to 80° C.

The dialkyltin oxide obtained in this process has an average particle diameter of 10 $\mu$m or more, and if the hydrolysis is performed under optimum conditions, there can be obtained particles of 50 $\mu$m or larger and almost uniform in size. Such large particles have never been obtained by the conventional processes, which usually produce particles not exceeding about 10 μm in diameter.

The control of the specific gravities of the three phases, which is another basic feature of this invention, may be attained by adding water, a basic substance, a salt, etc. to the resulting hydrolysis reaction mixture. Alternatively, it may be achieved by controlling beforehand the concentration of the basic substance, such as sodium hydroxide, potassium hydroxide, ammonium hydroxide, etc., in its aqueous solution to be used for the hydrolysis. The specific gravity of the organic phase can be controlled by selecting the organic solvent to be used in the hydrolysis. As the basic substance, sodium hydroxide is the most advantageous from the economical viewpoint. The specific gravity of the intermediate aqueous phase resulting from the hydrolysis can be controlled by controlling the concentration of the basic substance in its aqueous solution to be used in hydrolysis such that the resulting hydrolysis reaction mixture splits into distinct three phases, i.e., an upper, intermediate and lower phases containing tri-, mono- and dialkyltin oxides, respectively, each phase being substantially free from the other two oxides. The difference in specific gravity among the three phases is 0.02 or more.

For a better understanding of the features of this invention, the process of the present invention is explained below with reference to the drawings and in comparison with the method as described in U.S. Pat. No. 2,718,522.

Figure 4:
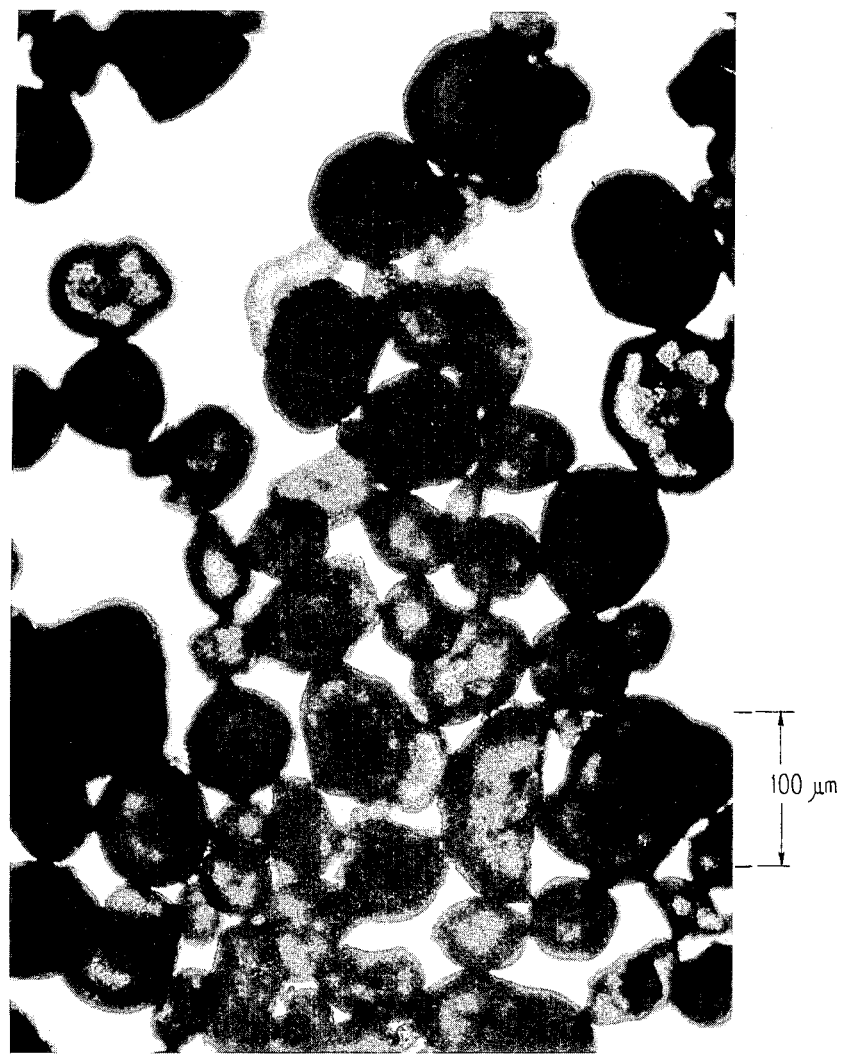
FIG. 4 is a microphotograph (enlargement: 100 magnifications) showing particles of di-n-butyltin oxide produced and isolated by the process of the present invention.
Figure 5:
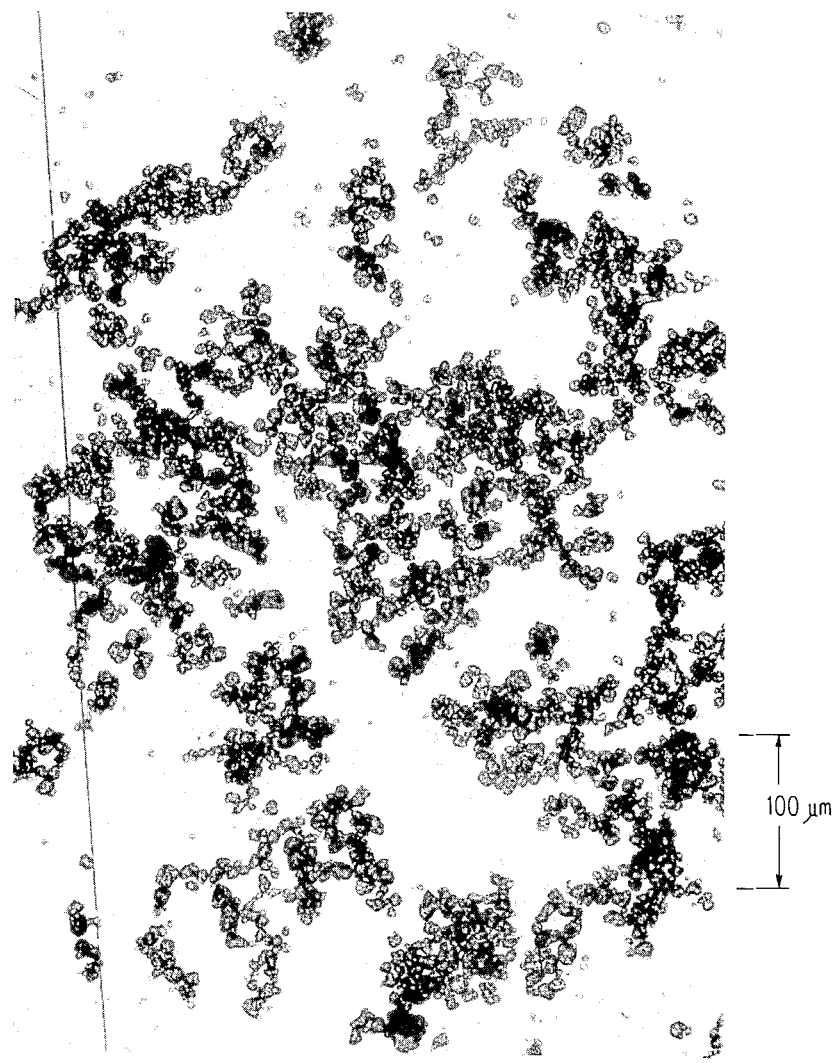
FIG. 5 is a microphotograph (enlargement: 100 magnifications) showing particles of di-n-butyltin oxide obtained by the method described in U.S. Pat. No. 2,718,522.

As shown in FIG. 1(a), according to the present invention, a mono-, di- or trialkyltin halide is subjected to hydrolysis under the specific conditions as explained hereinbefore, whereby the resulting reaction mixture splits into three phases. From the upper phase is isolated a bis(trialkyltin) oxide or a trialkyltin hydroxide; the intermediate phase is neutralized and then a monoalkyltin oxide is isolated therefrom; and a dialkyltin oxide is isolated from the lower phase. FIG. 2 shows the three phases formed by the split of a hydrolysis reaction mixture obtained in the process of this invention. The state of particles of di-n-butyltin oxide prepared by this process is shown in FIG. 4. On the other hand, according to the method of U.S. Pat. No. 2,718,522, a crude mixture of butyltin trichloride, dibutyltin chloride, tributyltin chloride and tetrabutyltin is treated with stannic chloride, thereby to react the tetrabutyltin to give a butyltin chloride compound, and the resulting compound is extracted to obtain an organic phase, which is hydrolyzed with alkali and then filtered to obtain dibutyltin oxide. A hydrolysis reaction mixture obtained in the same manner as that of the prior art gives two phases, as shown in FIG. 3, in which the upper turbid phase contains both the desired di-n-butyltin oxide and bis(tri-n-butyltin) oxide and the lower aqueous phase contains a salt. The state of particles of this prior art di-n-butyltin oxide is shown in FIG. 5. Comparisons between the two processes are summarized in the following Tables 1 and 2.

(1) Relationship between the state of hydrolysis reaction mixture and the average particle diameter of the di-n-butyltin oxide obtained:

TABLE 1

| Method | State of hydrolysis reaction mixture | Composition | Average particle diameter of DBTO |
|---|---|---|---|
| Present invention | three phases | upper Phase: toluene phase containing TBTO intermediate phase: aqueous phase containing salt lower phase: DBIO phase | 60 μm |
| Prior art | two phases | upper phase: turbid toluene phase containing DBTO and TBTO lower phase: aqueous phase containing salt | 8 μm |

Reaction conditions
Starting material: di-n-butyltin dichloride
Basic substance: 15% aqueous sodium hydroxide solution
Solvent: toluene
Temperature: 70° C.

(2) Relationship between the specific gravity the salt-containing aqueous phase and the splitting into phases:

TABLE 2

| | Present invention | Prior art method | |
|---|---|---|---|
| | (split into 3 phases) | (split into 2 phases) | (difficult to split) |
| Upper phase | TBTO phase (s.g. 1.1) | TBTO + DBTO phase (s.g. 1.1) | TBTO + DBTO phase (s.g. 1.1) |
| Intermediate phase | salt-containing aqueous phase (s.g. 1.18–1.26) | — | — |
| Lower phase | DBTO* phase (s.g. 1.3) | salt-containing aqueous phase (s.g. > 1.26) | salt-containing aqueous phase (s.g. < 1.18) |

Reaction conditions
Starting material: tri-n-butyltin chloride
Basic substance: aqueous sodium hydroxide solution
*The by-product DBTO had an average particle diameter of 30 μm.

In Tables 1 and 2 above, DBTO, TBTO and s.g. mean di-n-butyltin oxide, bis(tri-n-butyltin) oxide and specific gravity, respectively.

In preparing trialkyltin oxides according to the process of this invention, there is no need for the use of a solvent since the intended substances are liquids. The resulting hydrolysis reaction mixture is allowed to stand and, immediately after the initiation of the standing, the mixture splits into two phases, i.e., a salt-containing aqueous phase and an upper organic phase consisting substantially of a trialkyltin oxide. Then, the particles of a dialkyltin oxide present in the organic phase sediment, in the form of droplets accompanied by some part of the organic phase, through the salt-containing aqueous phase. After the completion of the sedimentation, there are given three distinct phases, i.e., an upper trialkyltin oxide phase, an intermediate aqueous phase and a lower dialkyltin oxide phase. The interfaces between the phases are so clear that each phase can be easily separated from one another by simple procedures.

The lower phase has good fluidity although the dialkyltin oxide content is about 50% or more, and hence it can be easily taken out of the vessel.

In the intermediate aqueous phase is dissolved a monoalkyltin oxide in the form of an alkali metal salt. High-quality monoalkyltin oxide may be isolated therefrom by precipitation with acid. However, if the amount is too large, the intermediate aqueous phase can be subjected as it is to biological treatment. After such treatments, the aqueous phase can be discharged as industrial waste water.

In the upper trialkyltin oxide phase, there is almost no dialkyltin oxide remaining, whose content is usually about 2,000 ppm or lower, showing that the two oxides have almost completely been separated. Hence, this upper phase is subjected to distillation etc. to remove a small amount of the water contained therein, followed by simple filtration to remove a small amount of a salt which has precipitated due to the distillation, thereby to obtain a high-quality trialkyltin oxide.

The di- and trialkyltin oxides in the lower phase can be easily separated and isolated by filtration. Alternatively, the lower phase may be treated as it is with a hydrohalogenic acid such as hydrochloric acid in a usual way to convert the oxides into the corresponding di- and trialkyltin halides, and the resulting halides are reacted with a tetraalkyltin to convert all of these into high-quality trialkyltin halides, which can be reused as a starting material.

In preparing dialkyltin oxides according to the process of this invention, the procedures are substantially the same as those with trialkyltin oxides except that since the intended substances are solids, an organic solvent is used for hydrolysis. In this case, by allowing the resulting hydrolysis reaction mixture to stand, it gives distinct three phases composed of an upper organic phase, an intermediate salt-containing aqueous phase and a lower dialkyltin oxide phase containing the solvent. Then, the three phases are separated from one another. From the organic phase, a trialkyltin oxide is obtained by removal of the solvent. From the salt-containing aqueous phase, a monolkyltin oxide is isolated by precipitation with acid. The lower phase has good fluidity although it has a high solid content, with the solvent content usually 40% or lower, and hence it can be easily taken out from the vessel. From the lower phase, a small amount of a salt contained therein is removed by water washing, and subsequently the organic solvent is removed by a proper means, such as vacuum drying, thereby to obtain a high-quality dialkyltin oxide.

The resulting mono- or trialkyltin oxide may be used as it is for various purposes. However, they can be converted into alkyltin halides, as mentioned hereinbefore with respect to the preparation of trialkyltin oxides, and then the resulting halides are reacted with a tetraalkyltin or a tetrahalogenotin to give high-quality dialkyltin halides, which can be reused as a starting material.

According to the present invention, the reaction mixture resulting from the hydrolysis of an alkyltin halide splits into three distinct phases respectively containing a mono-, di- and trialkyltin oxide, each phase being substantially free from the other two oxides. Accordingly, the phase containing a desired alkyltin oxide can be easily separated from the other phases by a simple procedure, and the product is easily obtained from the thus separated phase with high purity by a simple means. Therefore, the use of mechanical means of separation such as centrifugation or filtration, which has been essential for the separation of mono-, di- and trialkyltin oxides from hydrolysis reaction mixtures, can be omitted and, hence, all the problems accompanying the conventional processes and concerning workers' safety and health, environment and economical production can be solved.

The present invention will be illustrated in more detail with reference to the following examples, which should not be construed to limiting the scope of the invention.

EXAMPLE 1

A four-necked flask equipped with an overflow nozzle on the side wall was provided with a stirrer, a thermometer and a reflux condenser. To the flask were continously fed 3,850 g of a 20% aqueous solution of sodium hydroxide and 1,990 g of tri-n-butyltin chloride containing 4.8% di-n-butyltin dichloride, with stirring and heating at 50° C., to perform hydrolysis for 30 minutes. The resulting reaction mixture overflowed was allowed to stand. As a result, the contents split into three distinct phases, i.e., an upper bis(tri-n-butyltin) oxide phase, an intermediate aqueous phase containing a salt, and a lower di-n-butyltin oxide phase containing 48% bis(tri-n-butyltin) oxide. The di-n-butyltin oxide had an average particle diameter of 30 $\mu$m. The specific gravities of the upper, intermediate and lower phases were 1.1, 1.2 and 1.3, respectively. The three phases were separated from one another. The upper phase was dehydrated under reduced pressure, and then a small amount of a salt which had separated out was removed by filtration, thereby obtaining 1,629 g of bis(tri-n-butyltin) oxide. Hydrochloric acid titration revealed that its purity was 98.5%, and its theoretical yield based on the starting material was 89.4%.

EXAMPLE 2

The same apparatus as used in Example 1 was employed. To the flask were continuously fed 450 g of 30% aqueous sodium hydroxide solution and 300 g of tri-n-butyltin bromide containing 3.5% di-n-butyltin dibromide, with stirring and heating at 60° C., to perform hydrolysis for 60 minutes. To the resulting reaction mixture was added 260 g of water for specific gravity adjustment. The same precipitation as in Example 1 took place, and the reaction mixture split into three distinct phases. The specific gravity of the aqueous phase was measured and was found to be 1.25. Thereafter, the upper phase was treated in the same manner as in Example 1 to give 224.4 g (92.8% yield) of bis(tri-n- butyltin) oxide. Analysis revealed that the product was of high quality, its purity being 98.3% and the content of di-n-butyltin oxide dissolved therein being 300 ppm.

The lower phase weighed 12.5 g, which was occupied by 45% of di-n-butyltin oxide and 50% bis(tri-n-butyltin) oxide. This lower phase was subjected to vacuum filtration, and the resulting cake was washed with toluene and dried, thereby obtaining a white substance of di-n-butyltin oxide having an average particle diameter of 70 µm. Acid titration revealed that its purity was 99.2%.

The resulting filtrate and washings were put together and the toluene was distilled off, thereby obtaining bis(tri-n-butyltin) oxide as the residue. Analysis revealed that its purity was 96.3%. The total yield based on the starting material was 98.1%.

EXAMPLE 3

The same apparatus as used in Example 2 was employed. To the flask were continuously fed 220 g of 20% aqueous sodium hydroxide solution and 200 g of tri-n-octyltin iodide containing 6% di-n-octyltin diiodide, with stirring and heating at 70° C., to perform hydrolysis for 60 minutes. To the resulting reaction mixture were added 50 g of toluene and 148 g of water for specific gravity adjustment. As a result, the same precipitation as in Example 1 took place, and the reaction mixture split into three distinct phases. Thereafter, the toluene was distilled off from the upper phase in a usual way, thereby obtaining 141.0 g (88.5% yield) of bis(tri-n-octyltin) oxide. Analysis revealed that it was of high quality, its purity being 98.1%.

COMPARATIVE EXAMPLE 1

A four-necked flask was provided with a stirrer, a thermometer and a reflux condenser. Then, 385 g of 20% aqueous sodium hydroxide solution was introduced into the flask and heated to 50° C. 200 g of tri-n-butyltin chloride containing 4.8% di-n-butyltin dichloride was dropwise added thereto over a period of 30 minutes, and then, reaction was allowed to proceed at that temperature for an hour. The resulting reaction mixture was permitted to stand, whereby it split into a turbid organic phase and an aqueous phase, respectively having specific gravities of 1.15 and 1.2. However, the diameters of the thus-formed di-n-butyltin oxide particles were so small as to cause the interface to be in an indistinct emulsified state and, hence, separation of the two phases was difficult. The organic phase was a mixture of bis(tri-n-butyltin) oxide and di-n-butyltin oxide particles having an average particle diameter of 2 µm. Vacuum filtration was tried on this organic phase but the two oxides could not be separated. Hence, 5 g of acid clay was added to the organic phase as a filter aid, which was then filtered. 100 g of water was added to the resulting filtrate for washing, and the resulting organic phase was taken out and then dehydrated under reduced pressure, thereby obtaining 167 g of bis(tri-n-butyltin) oxide. Hydrochloric acid titration revealed that its purity was 96.3%, and its yield based on the starting material was 92%.

Although the resulting cake separated out as a mixture with acid clay contained all the di-n-butyltin oxide which had been formed during the reaction and an almost the same amount of bis(tri-n-butyltin) oxide, an economical method could not be found for the separation and isolation of the two oxides.

EXAMPLE 4

The same apparatus as used in Example 1 was employed. To the flask were continuously fed 1,075 g of 30% aqueous sodium hydroxide solution and 1,500 g of a cyclohexane solution which had been prepared by dissolving, in 750 g of cyclohexane, 750 g of di-n-butyltin dibromide containing 1.8% tri-n-butyltin bromide and 1.5% mono-n-butyltin tribromide. The above feeding was performed with stirring and heating at 70° C., to conduct hydrolysis for 45 minutes. To the resulting reaction mixture overflowed was added 3,600 g of water, and the mixture was then allowed to stand, whereby it split into three distinct phases. The specific gravities of the upper, intermediate and lower phases were 0.6, 1.1 and 1.3 respectively. The lower phase was separated out, washed with water, and then dried under reduced pressure, thereby obtaining 445 g of a white substance of di-n-butyltin oxide. Acid titration revealed that its purity was 99.8%, and the oxide had an average particle diameter of 50 µm.

The intermediate aqueous phase, which was transparence, was neutralized with carbon dioxide gas, whereby white crystals separated out. These crystals were washed with water and dried to obtain 5.5 of mono-n-butyltin oxide. Its purity was 96.1%.

From the upper phase, the cyclohexane was distilled off, thereby obtaining, as the residual liquid, 10.5 g of bis(tri-n-butyltin) oxide. Its purity was 95.8%. The total yield of all the butyltin oxides based on the starting material was 99.0%.

EXAMPLE 5

The same apparatus as used in Example 1 was employed. To the flask were continuously fed 1,300 g of 16% aqueous sodium hydroxide solution and 5,504 g of a toluene solution which had been prepared by dissolving, in 3,592 g of toluene, 1,912 g of di-n-butyltin dichloride containing 1.5% tri-n-butyltin chloride and 1.0% mono-n-butyltin trichlorine. The above feeding was performed with stirring and heating at 75° C., to conduct hydrolysis for 60 minutes. The resulting reaction mixture overflowed was allowed to stand, thereby splitting into three distinct phases. The specific gravities of the upper, intermediate and lower phases were 00.6, 1.1 and 1.2, respectively. These three phases were separated from one another and then subjected to the same treatments as in Example 4. As a result, the lower phase gave 1,520 g of di-n-butyltin oxide having a purity of 99.8% and an average particle diameter of 80 µm; the intermediate phase gave 2.6 g of mono-n-butyltin oxide having a purity of 95.9%; and the upper phase gave 5.9 g of bis(tri-n-butyltin) oxide having a purity of 95.6%. The total yield based on the starting material was 99.2%.

COMPARATIVE EXAMPLE 2

For comparison, the procedures in Example 5 were modified into conventional ones as follows. 130 g of 16% aqueous sodium hydroxide solution was heated to 75° C. 552 g of a toluene solution was dropwise added thereto, which had been prepared by dissolving, in 360 g of tolune, 192 g of di-n-butyltin dichloride containing 1.5% tri-n-butyltin chloride and 1.0% mono-n-butyltin trichloride. The above addition was performed with stirring at that temperature over a period of 2 hours, to conduct hydrolysis. The resulting reaction mixture was allowed to stand, thereby forming two phases, with the interface indistinct. The orgnanic phase was separated out, and di-n-butyltin oxide contained therein was separated from the toluene by means of vacuum filtration, which was very laborious and took as much as 2 hours. The thus-obtained white substance of di-n-butyltin oxide had an average particle diameter of 8 μm. In an attempt to remove a large amount of salts and bis(tri-n-butyltin) oxide, contaminating the above-obtained di-n-butyltin oxide, the product was put in a mixture of 200 g of toluene and 300 g of water, and the resulting mixture was stirred. Then the organic phase was separated out and subjected to filtration, but the recovery of the desired compound by filtration was almost impossible.

While the invention has been described in detail and with reference to specific embodiments thereof, it will be apparent to one skilled in the art that various changes and modification can be made therein without departing from the spirit and scope thereof.

What is claimed is:

1. A process for the fractional production of alkyltin oxides which comprises for the steps of:
    subjecting a mono-, di- or trialkyltin halide to continuous hydrolysis at a temperature between 30° to 100° C. for a period of 10 minutes to 3 hours by the use of a 1% to 50% aqueous solution of a basic substance, thereby forming in the hydrolysis reaction mixture a dialkyltin oxide having an average particle diameter of 10 μm or more, provided that where an intended alkyltin oxide is solid, the continuous hydrolysis is performed in the presence of an organic solvent slightly soluble in water and having a boiling point as measured under ordinary pressure of 150° C. or lower and a specific gravity of 1.1 or smaller;
    allowing the resulting reaction mixture to stand, thereby to form three phases composed of an organic phase, an aqueous phase, and a phase consisting substantially of the dialkyltin oxide and having a specific gravity 0.02 or more larger than that of the aqueous phase;
    separating the three phases from one another; and
    isolating a bis(trialkyltin) oxide or a trialkyltin hydroxide from the organic phase, a monoalkyltin oxide from the aqueous phase, and the dialkyltin oxide from the phase consisting substantially of the dialkyltin oxide and having a specific gravity 0.02 or more larger than that of the aqueous phase.

* * * * *